United States Patent [19]

Rexroth

[11] Patent Number: 4,550,727
[45] Date of Patent: Nov. 5, 1985

[54] ELECTROSURGICAL GENERATOR
[75] Inventor: Frederick W. Rexroth, Dunedin, Fla.
[73] Assignee: Medical Research Associates, Ltd. #2, Clearwater, Fla.
[21] Appl. No.: 512,044
[22] Filed: Jul. 8, 1983

Related U.S. Application Data

[63] Continuation-in-part of Ser. No. 447,808, Dec. 8, 1982, Pat. No. 4,473,075.

[51] Int. Cl.⁴ ............................................. A61B 17/39
[52] U.S. Cl. ............................ 128/303.14; 128/303.17
[58] Field of Search ...................... 128/303.13, 303.14, 128/303.17

[56] References Cited

U.S. PATENT DOCUMENTS

| | | | |
|---|---|---|---|
| 3,937,214 | 2/1976 | Hutchins, IV | 128/630 |
| 4,188,927 | 2/1980 | Harris | 128/303.17 |
| 4,318,409 | 3/1982 | Oosten | 128/303.17 |
| 4,429,694 | 2/1984 | McGreevy | 128/303.17 |

Primary Examiner—Kyle L. Howell
Assistant Examiner—Ruth S. Smith
Attorney, Agent, or Firm—Epstein & Edell

[57] ABSTRACT

An electrosurgical generator, having particular utility in surgical procedures on human joints, is provided with an output impedance in the range of 600 to 2,500 Ohms in order to efficiently transfer energy to the high impedance joint. The relatively high output impedance permits much lower power settings to be empolyed than are required by conventional electrosurgical generators so that little or no damage results in surrounding tissue. In the preferred embodiment, the output impedance range is 900 to 1,400 Ohms and is provided by an isolation transformer in which the turns ratio is selected to obtain the desired generator output impedance across the transformer secondary winding.

9 Claims, 4 Drawing Figures

ELECTROSURGICAL GENERATOR

CROSS-REFERENCE TO RELATED APPLICATIONS

The present application is a continuation-in-part of my U.S. patent application Ser. No. 06/447,808, filed Dec. 8, 1982 now U.S. Pat. No. 4,473,075 and entitled "Electrosurgical Generator With Improved Rapid Start Capability". The disclosure in that patent application is expressly incorporated herein by reference.

The invention described herein is also an improvement of the Electrosurgical Generator described and illustrated in U.S. Pat. No. 4,318,409 to Oosten, the disclosure of which is also expressly incorporated herein by reference in its entirety.

BACKGROUND OF THE INVENTION

1. Technical Field

The present invention relates to electrosurgical generators and, more particularly, to electrosurgical generators having specific utility in arthroscopic surgical procedures.

2. Discussion of the Prior Art

My aforementioned U.S. patent application Ser. No. 06/447,808 describes an electrosurgical generator which is advantageously useful for arthroscopic surgical procedures at human joints having higher impedance than the 500 Ohms or less of other human tissue sites at which electrosurgical generators have been conventionally employed. Specifically, I describe in that patent application an electrosurgical generator having an output impedance of 1,000 Ohms or greater in order to more closely match the impedance of the human joint. I further describe the problem presented by improper matching of the generator impedance to the human joint at the surgical site, namely: the generator does not efficiently transfer energy to the site, thereby requiring higher power settings at the generator. These higher power settings result in tissue damage, such as necrosis, in the surrounding tissue. My aforesaid patent application further indicates that a generator impedance of 1,000 Ohms or more should be provided to more properly match the impedance of the human joint.

I have now found that the impedance at human joints at which electrosurgery can be employed may vary over a considerably wider range than described in my aforesaid patent application.

OBJECTS AND SUMMARY OF THE INVENTION

It is, therefore, an object of the present invention to provide an electrosurgical generator which efficiently transfers energy to human joint surgical sites made up of relatively high impedance bony substances, cartilage, meniscus, and the like.

Another object of the present invention is to provide an electrosurgical generator with an output impedance selected to efficiently transfer energy to a human joint surgical site at the lowest possible generator power setting and without burning or otherwise damaging surrounding tissue.

Still another object of the present invention is to provide a method for performing electrosurgery with a minimum amount of electrical energy.

I have found that an electrosurgical generator for use with human joint surgical sites should have an output impedance in the range of 600 to 2,500 Ohms to more efficiently transfer energy to the site without damage to the surrounding tissue. In the preferred embodiment, this range is from 900 to 1,400 Ohms. The desired impedance is achieved by matching the impedance of the output isolation transformer to the joint tissue impedance at the surgical site, and is established by the turns ratio between the primary and secondary windings of the transformer. In the preferred embodiment, a step-up transformer is employed with a toroidal core about which electrically insulated primary and secondary windings are wound and separated by an insulating layer of tape, or the like. The primary winding is connected in parallel with an impedance-determining parallel RC circuit.

BRIEF DESCRIPTION OF THE DRAWINGS

The above and still further objects, features and advantages of the present invention will become apparent upon consideration of the following detailed description of specific embodiments thereof, especially when considered in conjunction with the accompanying drawings wherein like parts in each of the several figures are identified by the same reference numerals, and wherein.

DESCRIPTION OF THE PREFERRED EMBODIMENTS

Figure 1:
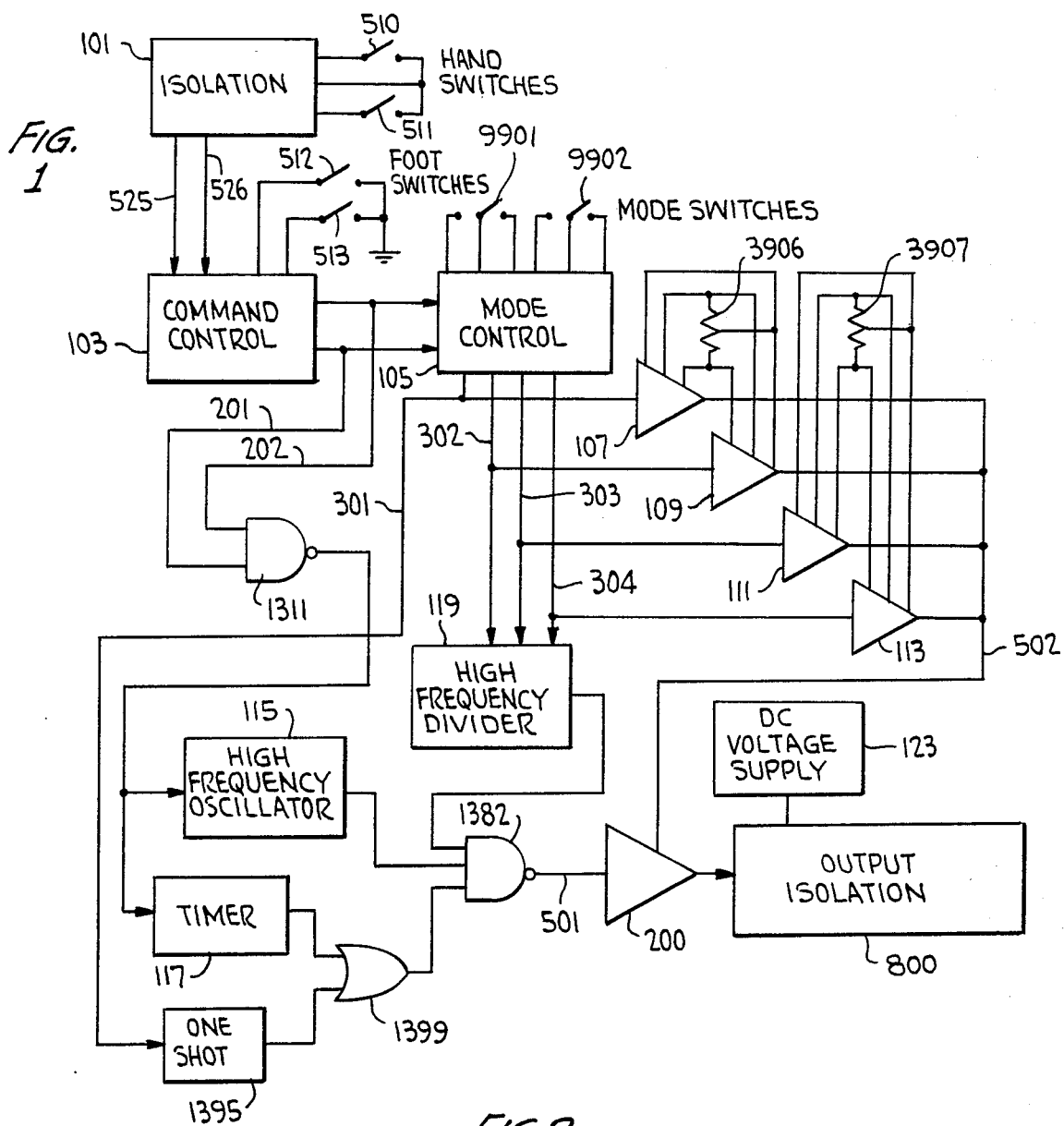
FIG. 1 is a partial functional block diagram and partial circuit schematic diagram showing an electrosurgical generator of the type with which the present invention is useful.

The functional block diagram illustrated in FIG. 1 is substantially identical to the functional block diagram in FIG. 1 of my aforementioned U.S. patent application Ser. No. 06/447,808. The following description corresponds to the description of that functional block diagram in my aforesaid patent application and is repeated here for ease of reference only. The detailed circuitry and description thereof may be found in that patent application which is expressly incorporated herein by reference in its entirety.

Referring specifically to FIG. 1, an electrosurgical generator is shown as being operable in four alternatively selectable modes in which four respective output signals are generated, namely a pure cut signal, a blend signal, a fulgurate signal and a desiccated signal. These four modes of operation can be subdivided into two command groups. The first group, which may be referred to as the cut command group, includes the pure cut and blend mode. The second group, which may be referred to as the coagulate command group, includes the fulgurate and desiccate modes. A treating physician may continuously select either the cut command or the coagulate command by using hand switches 510 and 511, or foot switches 512 and 513. The hand switches, which are most likely to come into electrical contact with the patient or physician during normal use, are isolated from the bulk of the electrical circuit by isolation unit 101. If both the cut and coagulate commands are selected simultaneously by the physician, the command control 103 acts to terminate all functions until the command ambiguity is resolved. Absent such ambiguity, the command control unit 103 activates command line 201 if the cut command is chosen, or command line 202 if the coagulate command is chosen.

The activated command line energizes a corresponding circuit in the mode control unit 105, which circuit is controlled by either of the two mode switches 9901 and 9902. Switch 9901 is associated with the cut command line 201 and permits the operator to choose between two cut modes, namely pure and blend. Switch 9902 is associated with the coagulate command line 202 and permits the operator to choose between two coagulate modes, namely desiccate and fulgurate. Only one of the two command lines 201 and 202 may be active at any time. Therefore, only one of the four mode output lines 301, 302, 303 and 304 from mode control unit 105 are active at any time. Mode line 301 is active for the pure cut mode, mode line 302 is active for the blend mode, mode line 303 is active for the desiccate mode, and mode line 304 is active for the fulgurate mode.

The active mode line enables a respective output control amplifier 107, 109, 111 and 113. These amplifiers provide a voltage which controls the output gain of the main output amplifier 200. Amplifiers 107 and 109 control the cut mode output levels and are controlled by a potentiometer 3906. Amplifiers 111 and 113 control the output level for two coagulate functions and are controlled by potentiometer 3907.

Activation of either of the two command lines 201 or 202 causes NAND gate 1311 to activate the fixed high frequency oscillator 115 and the secondary modulation timer/oscillator 117. The output of the fixed high frequency oscillator 115, which is preferably at a frequency of 475 KHz, is gated through NAND gate 1382 to main amplifier 200. Variable high frequency divider 119 provides the primary modulation of the high frequency signal by counting output pulses of the fixed high frequency oscillator 115 and periodically interrupting the output of NAND gate 1382 in accordance with prescribed counting logic.

The output of NAND gate 1382 is also periodically interrupted by the signal from oscillator/timer 117 to provide a secondary modulation of the high frequency signal at gate 1382. The timer/oscillator 117 operates at a fixed frequency which is very much lower than the fixed frequency of the high frequency oscillator 115. Typically, the frequency of the signal provided by oscillator/timer 117 is 250 Hz.

In the pure cut mode, the onset of the pure cut command signal at line 301 triggers a one-shot multivibrator 1395 which responds with a pulse of predetermined duration that is passed through OR gate 1399 to another input of NAND gate 1382. For the duration of the predetermined interval of the one-shot puse, the effect of the low frequency modulation signal from timer 117 is negated at NAND gate 1382 so that the high frequency signal from oscillator 115 passes through that gate without secondary modulation. Upon termination of the output pulses from one-shot mutlivibrator 1395, the cyclic waveform from oscillator/timer 117 controls passage of the high frequency signal from oscillator 115 through gate 1382. Therefore, for the pure cut mode, there is a delay, controlled by one-shot multivibrator 1395, before secondary modulation is applied to the high frequency signal. The secondary modulation is only applied during the steady state portion of the pure cut mode and not during the initial start-up portion of that mode. This technique provides the extra energy level required to initiate and incise quickly without having to sustain that high energy level throughout the duration of the incision. One-shot multivibrator 1395 is only actuated during the start of a portion of the pure cut mode and does not affect operation in any of the other three modes.

The output signal from NAND gate 1382 is fed to the input of main amplifier 200. As previously noted, the output level of the main amplifier 200 is set by the output signals from the activated output controlled amplifier 107, 109, 111 or 113. The main amplifier output signal draws current from the d.c. voltage source 123 through the output isolation unit 800. It is in this output isolation unit 800 that the present invention resides.

Figure 2:
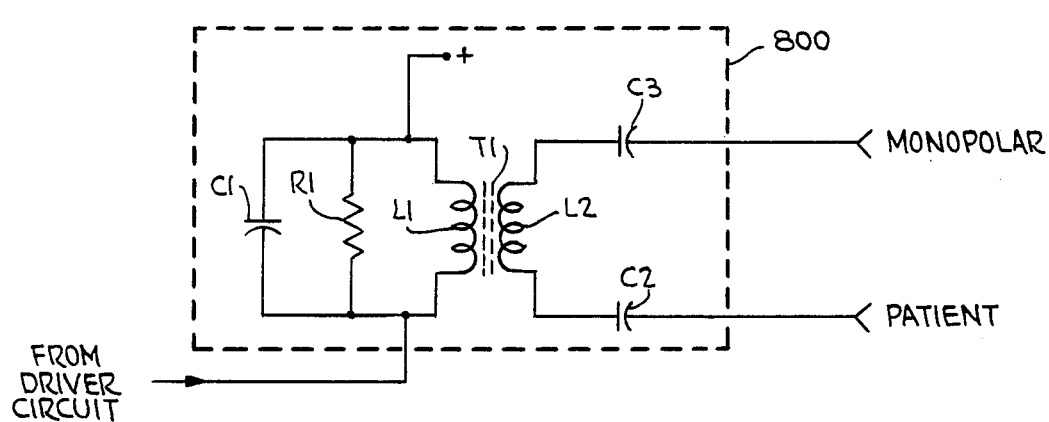
FIG. 2 is a schematic diagram of an output circuit constructed in accordance with the present invention.

The output circuit 800 is illustrated in detail in FIG. 2 to which specific reference is now made. This circuit receives its input signal from a constant current amplifier stage corresponding to the main output amplifier 200 of FIG. 1. This input signal is applied to one side of a tank circuit comprising capacitor C1, resistor R1 and the primary winding L1 of an isolation transformer T1. These parallel-connected elements form a resonant circuit, the resonance being at a frequency which is lower than the 475 KHz of the high frequency signal generated at high frequency oscillator 115. The other side of the tank circuit is coupled to a d.c. voltage supply which is typically at +180 volts. By tuning the tank circuit to a frequency lower than the high frequency pure cut signal, the amplitude of all of the pulses in each pulse burst is limited, with the exception of the final pulse which is free to ring to its maximum peak amplitude. The secondary winding L2 has one side thereof connected through series capacitor C2 to the patient ground terminal. The other side of secondary winding L2 is connected through series capacitor C3 to the monopolar output terminal.

In accordance with the present invention, the output impedance reflected in the secondary circuit across the monopolar and patient ground terminals resides in the impedance range from 600 to 2,500 Ohms. In most cases, this range can be narrowed to 900 to 1,400 Ohms. For a particular application, the impedance of the primary circuit comprising elements C1, R1, and L1 is reflected at the proper impedance value in the output circuit by appropriately choosing the turns ratio between primary winding L1 and secondary winding L2. In a typical example, wherein the desired output impedance is between 1,100 and 1,200 Ohms at 475 KHz, the turns ratio of transformer T1 may be 1:6. For that embodiment, capacitor C1 has a capacitance of 12,000 pf, resistor R1 has a resistance of 500 Ohms and primary winding L1 includes ten turns wound about a core having an inductance of 846 microHenries per 100 turns.

The output circuit of FIG. 2 may be seen to provide both electrical isolation and an efficient matching of impedance to the surgical site. The isolation prevents shock hazard for the patient and the physician. The impedance matching permits efficient transfer of energy to the surgical site at relatively low operating energy settings.

Figure 3:
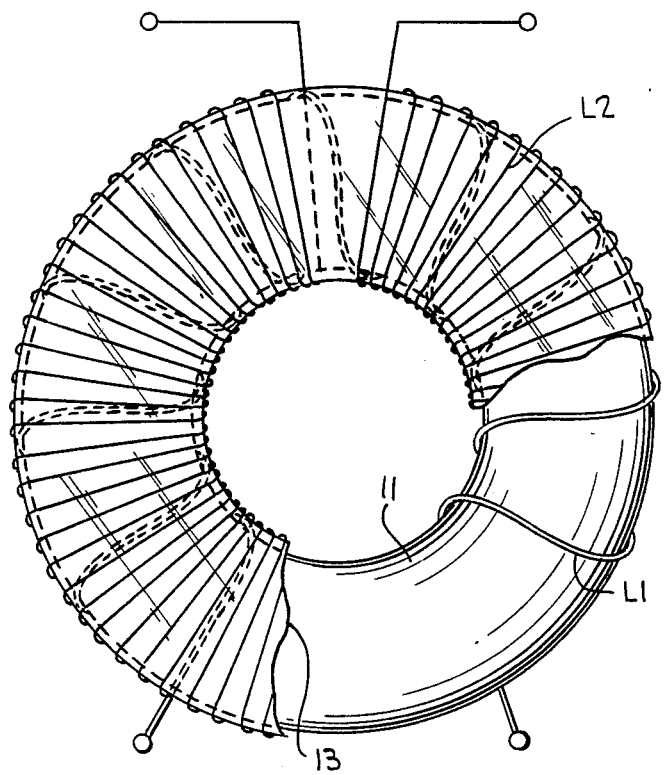
FIG. 3 is a view in plan of an output transformer constructed in accordance with the principles of the present invention.

A typical output transformer T1 is illustrated in FIG. 3 to which specific reference is now made. A toroidal core 11 may, for example, be the core manufactured and sold by Arnold Engineering of Marengo, Illinois, as Part No. FE-2500-0101. Primary winding L1 includes ten turns of #22 AWG wire having an insulated sleeve.

The wire for winding L1 is wound helically about core 11 with the insulating sleeve in direct contact with the core. At least one layer of insulating tape 13 is wound about primary winding L1, helically about the core, so as to provide an electrical insulating layer which leaves only the ends of primary winding L1 exposed. Secondary winding L2 is wound about the core 11 outside insulating tape 13. Secondary winding L2 also has an electrical insulating sleeve disposed thereabout and is #22 AWG wire. The insulating sleeve about the wires combine with the insulating tape 13 to provide three layers of insulation between the wires. In the embodiment illustrated, primary winding L1 has ten turns about core 11 whereas winding L2 has sixty turns, thereby providing a step-up ratio of 1:6.

Figure 4:
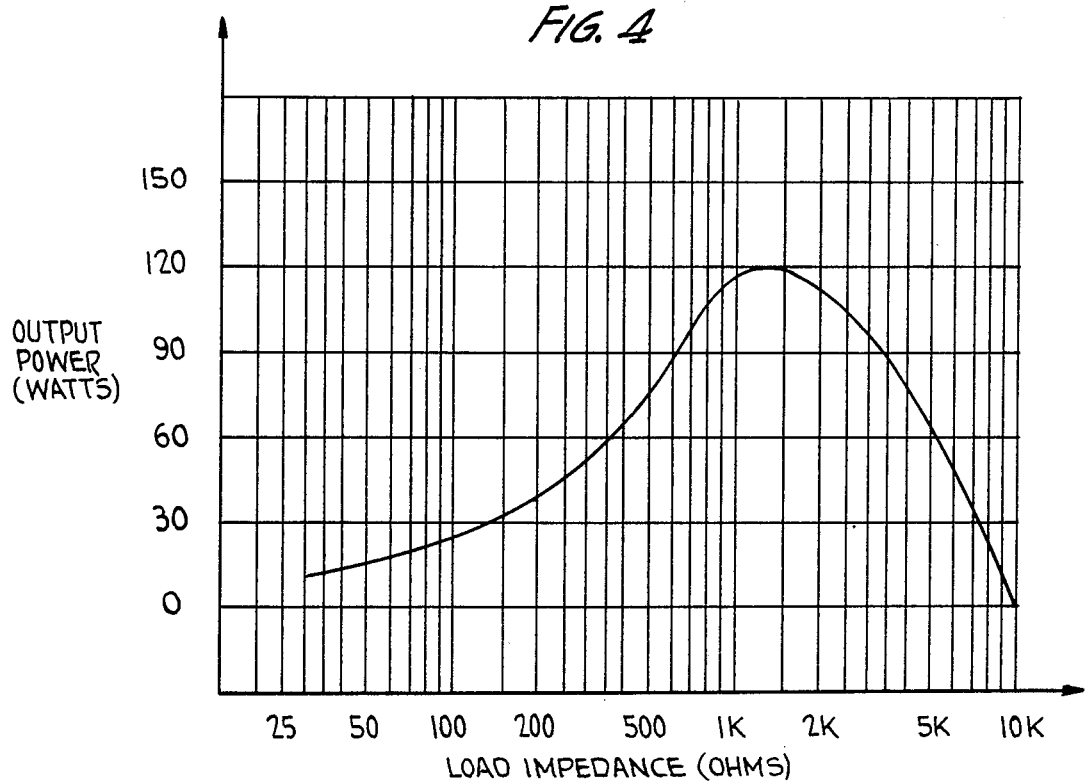
FIG. 4 is a graphical plot of the output power versus load resistance of a typical output circuit in accordance with the present invention.

Referring to FIG. 4, a plot of the output power, in watts, versus the load impedance, in Ohms is provided for the pure cut mode of operation with a typical knee joint load. It is noted that the output power is maximum in the range between 600 and 2,500 Ohms. Therefore, an output impedance for circuit 800 within this range results in optimum energy transfer from the electrosurgical generator to the load. An even narrower range of impedances, between 1,100 and 1,400 Ohms is seen to provide an even higher output power range. Therefore, the turns ratio of transformer T1 is, according to the present invention, adjusted until the output impedance of circuit 800 corresponds to the load impedance which provides a maximum, or close to maximum, output power.

In the preferred embodiment described hereinabove, wherein the Arnold Engineering toroid core FE-2500-0101 model is employed, the outside diameter of the core is 2.5 inches, the inside diameter is 1.25 inches, and the thickness is one inch. The permeability of that core is 25 and its inductance is 846 micro-Henries per 100 turns. The mean magnetic path is 14.96 centimeters and the core is made out of powdered iron. It is to be understood that these parameters represent only a preferred embodiment and should not be construed as limiting the broader aspects of the present invention.

From the foregoing description, it will be appreciated that the invention makes available a novel electrosurgical generator and method for performing the electrosurgery wherein optimum power transfer from the generator to a human joint surgical site is possible.

Having described a preferred embodiment of a new and improved electrosurgical generator constructed in accordance with the present invention, it is believed that other modifications, variations and changes will be suggested to those skilled in the art in view of the teachings set forth herein. It is, therefore, to be understood that all such variations, modifications and changes are believed to fall within the scope of the present invention as defined by the appended claims.

What is claimed is:

1. An electrosurgical generator for delivering a high frequency cutting signal to a surgical site comprising a human joint having a first impedance, without damaging softer tissue having a second lower impedance and surrounding said joint, said electrosurgical generator comprising:

actuable source means responsive to application of a control signal thereto for providing a high frequency cutting signal;

terminal means responsive to application of said high frequency cutting signal thereto for delivering the applied cutting signal to said surgical site;

selectively actuable control means for providing selective application of said control signal to said source means; and impedance matching means interposed between said source means and said terminal means for establishing the effective output impedance of said source means, said effective output impedance being selected to be substantially equal to said first impedance and substantially higher than said second impedance such that said source means efficiently transfers energy in said cutting signal to said joint and transfers comparatively negligible energy to said surrounding tissue;

wherein said first impedance is in the range between 1100 and 1400 ohms;

wherein said impedance matching means is a transformer circuit having an output impedance value equal to said first impedance;

said electrosurgical generator further comprising:

rapid start means responsive to said control signal for applying said high frequency cutting signal to said terminal means continuously for a predetermined time interval; and further means responsive to expiration of said predetermined time interval for cyclically and alternatively applying and inhibiting application of said high frequency cutting signal to said terminal means such that each cycle of application and inhibition is very much shorter than said predetermined time interval.

2. The electrosurgical generator according to claim 1 wherein said predetermined time interval is in a range of 100 to 500 milliseconds, and wherein the time duration of each cycle of application and inhibition is in a range of 1 to 20 milliseconds.

3. The electrosurgical generator according to claim 1 further comprising:

timer means for generating a repetitive gating signal which alternates cyclically between first and second amplitude levels;

wherein said further means comprises gating means connected to receive said repetitive gating signal and said high frequency signal, responsive to activation of said cut command signal for passing said high frequency signal when said gating signal is at said first amplitude level and inhibiting passage of said high frequency cutting signal when said gating signal is at said second amplitude level; and wherein said rapid start means comprises first means responsive to said control signal for generating an inhibit signal for said predetermined time interval, said second means being responsive to said inhibit signal for inhibiting application of said gating signal to said gating means while instead applying a further signal at said second amplitude to said gating means.

4. The electrosurgical generator according to claim 1 wherein said transformer circuit comprises isolation transformer means having a primary winding and at least one secondary winding, and wherein said output impedance value is presented across said secondary winding.

5. The electrosurgical generator according to claim 4 wherein said transformer circuit includes a toroidal core member, wherein said primary winding includes a first wire wound toroidally about said core member a first predetermined number of times, wherein said secondary winding includes a second wire wound about said core member a second predetermined number of times, and wherein said second predetermined number is greater than said first predetermined number.

6. The electrosurgical generator according to claim 5 further comprising a resistor and a capacitor connected in parallel with each other and across said primary winding.

7. The electrosurgical generator according to claim 6 wherein said resistor has a resistance of 500 Ohms, wherein said capacitor has a capacitance of 12,000 picofarads, and wherein said first predetermined number is one-sixth of said second predetermined number.

8. The electrosurgical generator according to claim 7 wherein said core member has an inductance of approximately 846 micro-Henries per 100 turns.

9. The electrosurgical generator according to claim 5 further comprising:
first electrical insulating sleeve means disposed about said first wire and positioned in contact with said core member;
electrical insulating tape means wrapped about said first wire and said core member; and
second electrical insulating sleeve means disposed about said second wire;
wherein said second wire in said second insulating sleeve means is wound about said electrical insulating tape means.

* * * * *